United States Patent [19]
Bankier et al.

[11] Patent Number: 5,846,493
[45] Date of Patent: Dec. 8, 1998

[54] SYSTEM FOR ANALYZING A SUBSTANCE FROM A SOLUTION FOLLOWING FILTERING OF THE SUBSTANCE FROM THE SOLUTION

[75] Inventors: Jack D. Bankier, Northbrook; Philip M. Cashmer, Addison, both of Ill.

[73] Assignee: Promega Corporation, Madison, Wis.

[21] Appl. No.: 388,604

[22] Filed: Feb. 14, 1995

[51] Int. Cl.⁶ ................................................... B01L 11/00
[52] U.S. Cl. ........................ 422/101; 210/406; 422/102; 435/288.4; 435/305.2; 435/308.1
[58] Field of Search ................... 422/101, 102; 210/445, 232, 482, 406; 435/305.2, 308.1, 286.6, 287.1, 288.4, 288.5

[56] References Cited

U.S. PATENT DOCUMENTS

| | | | |
|---|---|---|---|
| 4,160,803 | 7/1979 | Potts | 422/101 |
| 4,902,481 | 2/1990 | Clark et al. | 422/101 |
| 5,141,719 | 8/1992 | Fernwood et al. | 422/101 |
| 5,205,989 | 4/1993 | Aysta | 422/101 |
| 5,219,528 | 6/1993 | Clark | 422/101 |
| 5,264,184 | 11/1993 | Aysta | 422/101 |
| 5,417,923 | 5/1995 | Bojanic et al. | 422/101 |

*Primary Examiner*—Jan Ludlow
*Attorney, Agent, or Firm*—Grady J. Frenchick; Stroud, Stroud, Willink, Thompson & Howard; Karen B. King

[57] ABSTRACT

A system is provided for filtering a substance from a solution for subsequent analysis of the substance. The system has a manifold and a removable cover capable of latching onto a base defining an interior of the manifold. Apertures are formed in the cover capable of receiving columns having a filter for filtering the substance from the solution as solution is drawn through the columns into the manifold. The columns may be integrally formed to provide a set of columns. As a result, an array of apertures can receive a number of sets of columns to conduct the filtering process.

15 Claims, 4 Drawing Sheets

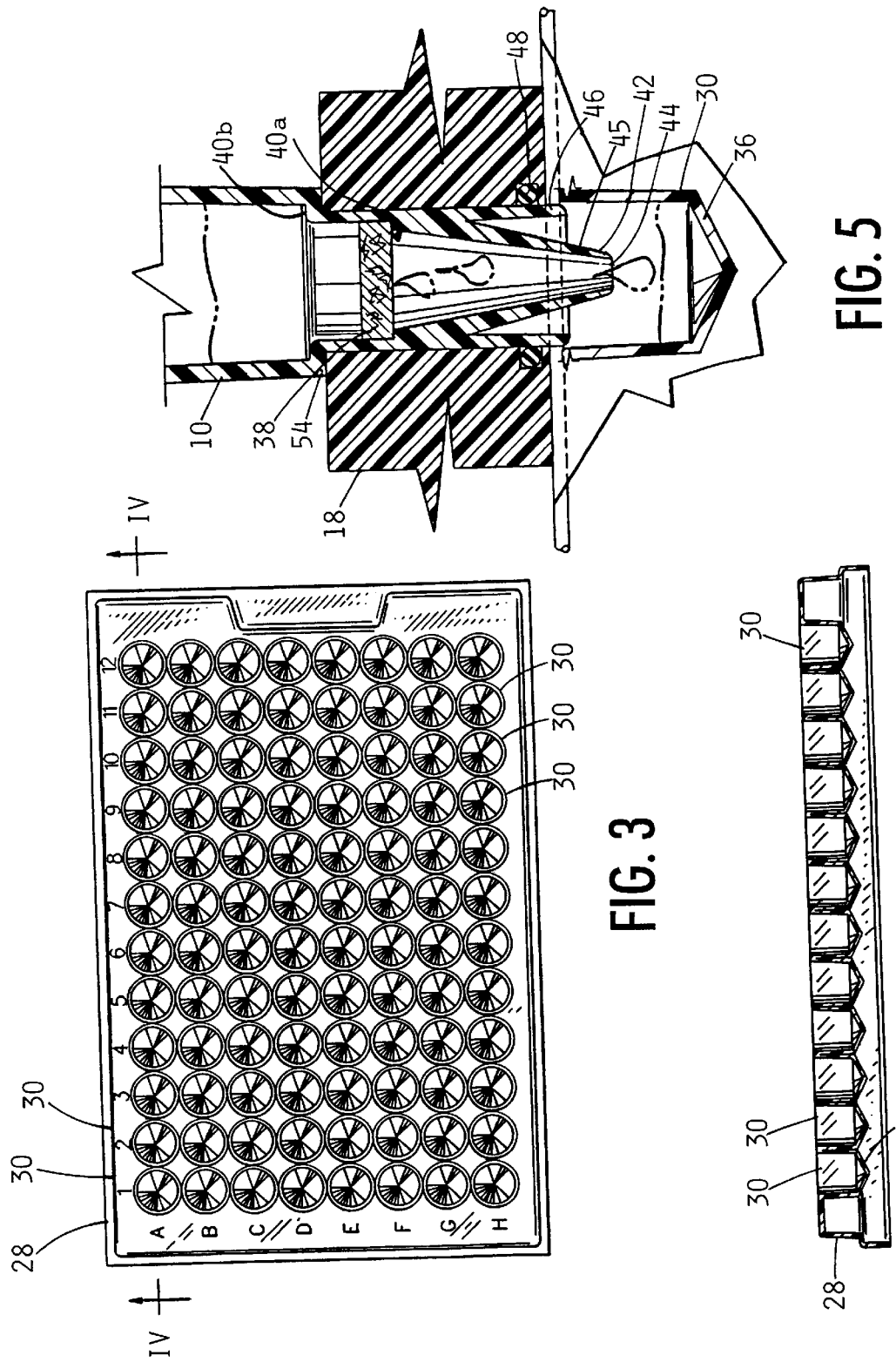

SYSTEM FOR ANALYZING A SUBSTANCE FROM A SOLUTION FOLLOWING FILTERING OF THE SUBSTANCE FROM THE SOLUTION

BACKGROUND OF THE INVENTION

The present invention generally relates to a system and a method for filtering a sample from a solution. More specifically, the present invention relates to a system and a method for filtering deoxyribonucleic acid (DNA) from a solution contained within a syringe or other dispenser containing DNA as part of the solution.

Filtering systems for reclaiming DNA are, of course, generally known. One such system is generally described in commonly assigned U.S. patent application Ser. No. 07/923,776 filed Aug. 3, 1992, now abandoned. Other prior art systems are also known. However, many of the prior art systems are ineffective in reclaiming the DNA from the solutions. Currently, many systems only have a reclamation rate or effectiveness of approximately eighty percent (80%).

DNA analysis is typically used to establish quantitative theories relating to biological phenomena, such as relationship to a specific disease. Often, only a small portion of a DNA sample is defective. If only a small percent of the DNA can be reclaimed, a significant possibility exists that the defective portion of the DNA sample could be in that part of the sample that could not be claimed by prior filtering systems. It is, therefore, critical to reclaim as much DNA as possible from a given solution so as to be able to identify any defective portions within the sample.

A need, therefore, exists for an improved system and a method for reclaiming DNA or other substances from a solution containing the DNA or other substance.

SUMMARY OF THE INVENTION

The present invention provides an improved system and a method for reclamation of a sample, such as DNA, from a solution. To this end, the present invention provides a system and a method for drawing a solution containing the sample through a container holding the solution and a filter assembly sealingly engaged thereto.

To this end, in an embodiment, a system is provided for filtering a substance for analysis from a solution. The system has a manifold having an interior defined by a base portion and a cover wherein the cover is removably secured to the base. A plurality of apertures extend through the cover. A plurality of columns receives the solutions with the substance through an inlet end of each of the plurality of columns and dispenses solution without the substance through an outlet end of each of the plurality of columns wherein the solution is fed into the interior of the manifold and further wherein each of the plurality of columns is mounted on the corresponding one of the plurality of apertures.

In an embodiment, a filter is provided in each of the plurality of columns capable of capturing the substance from the solution as the solution is fed into the interior of the manifold.

In an embodiment, at least two of the plurality of columns are integrally formed to form a set of columns.

In an embodiment, the plurality of apertures extending through the cover define an array of rows of the apertures wherein at least a portion of the plurality of columns form a set wherein the number of columns in the set is defined by the number of rows in the array.

In an embodiment, a latch couples the base portion on the manifold to the cover.

In an embodiment, a seal is constructed and arranged between the cover and the base portion of the manifold.

In an embodiment, an inlet is connected to the base portion and is capable of receiving a connector to provide vacuum pressure to the interior of the manifold.

In an embodiment, a ledge is formed on an interior wall of the base portion within the interior of the manifold.

In an embodiment, a dish defines a plane having a plurality of containers corresponding to the plurality of apertures in the cover wherein the dish is capable of placement in the interior of the manifold. The dish may include designators assisting in identifying each of the plurality of containers in the dish.

In an embodiment, an O-ring is provided in an interior wall of each of the plurality of apertures.

In an embodiment, a conical tip leads to the outlet end of each of the plurality of columns.

In an embodiment, the substance for analysis by the system is DNA.

In another embodiment of the present invention, a method is provided for filtering a substance for analysis from the solution. The method comprises the steps of: providing a manifold having an interior having a cover; providing a plurality of apertures extending through the cover; securing a column to each of the plurality of apertures; feeding solution including the substance into each of the columns; and providing a vacuum to the manifold to draw the solution into the interior of the manifold without the substance.

In an embodiment, the method further comprises the step of integrally forming at least a portion of the columns to form a set of the columns.

In an embodiment, the method further comprises the step of providing a dish in the interior of the manifold. The method further comprises filtering the substance into the dish.

In an embodiment, the method further comprises the step of providing a filter in each of the columns through which the solution passes, but not the substance.

In an embodiment, the method further comprises the step of providing a latch to secure the cover of the manifold to the remainder of the manifold to form the interior.

In another embodiment of the present invention, a filter assembly for removing a substance from a solution is provided. The filter assembly comprises a plurality of columns integrally formed as a unit wherein each of the plurality of columns has a first opening at one end capable of receiving the solution with the substance and a second opening at an opposite end capable of dispensing the solution without the substance. A filter is press-fit into each of the plurality of columns wherein each of the plurality of filters prevents the substance from passing through the opening at the opposite end of each of the plurality of columns.

In an embodiment, the filter assembly has a tapering wall defining a top portion of each of plurality of columns.

In an embodiment, the filter assembly has a conical tip defining a lower portion of each of the plurality of columns.

In an embodiment, the first opening of each of the columns is larger than each of the second openings.

In an embodiment, the filter assembly has a ledge between a top portion and a bottom portion of each of the plurality of columns wherein the filter is press-fit into the bottom portion of each of the plurality of columns. A conical tip extends within the bottom portion beyond an end of the bottom portion. The top portion is substantially evenly tapered and the bottom portion has a set of substantially equal diameters throughout its length.

In an embodiment, the filter assembly has a connector section integrally formed between the top portion of adjacent columns to maintain the columns in substantially parallel alignment.

In an embodiment, the plurality of columns of the filter assembly is at least three.

In yet another embodiment of the present invention, a dish is provided for collecting a substance for analysis. The dish has an integrally molded planar surface having a plurality of apertures therein wherein the plurality of apertures form an array in which a container integrally extends from each of the plurality of apertures capable of collecting the substance in each of the containers.

In an embodiment, designators identity each of the plurality of apertures of the array. The designators may be numerical and/or alphabetic.

In an embodiment, the dish has a conical tip forming a base of each of the containers.

It is, therefore, an advantage of the present invention to provide a system and a method for filtering a substance from a solution.

Another advantage of the present invention is to provide a system and a method for simplifying the process of filtering DNA from a solution for subsequent analysis of the DNA sample.

A still further advantage of the present invention is to provide a system and a method which implement integrally formed columns in which the DNA samples are filtered from the solution.

Yet another advantage of the present invention is to provide a system and a method that is compactly arranged for filtering substances from a solution.

Moreover, an advantage of the present invention is to provide a system and a method that maintains a seal between all components during the filtering process.

And, an advantage of the present invention is to reclaim nearly one-hundred percent of the substance through the filtering system and method of the present invention.

Additional features and advantages of the present invention are described in, and will be apparent from, the detailed description of the presently preferred embodiments and from the drawings.

BRIEF DESCRIPTION OF THE DRAWINGS

FIG. 3 illustrates a top plan view of an embodiment of a component of a filtering system of the present invention.

FIG. 4 illustrates a cross-sectional view taken generally along the line IV—IV of FIG. 3.

FIG. 5 illustrates a partial sectional view of an embodiment of a component of the filtering system of the present invention.

DETAILED DESCRIPTION OF THE PRESENTLY PREFERRED EMBODIMENTS

The present invention provides a system and a method for filtering a sample, such as DNA, from a solution so as to separate the sample for further desired analysis or utilization. Such a system is generally illustrated in FIGS. 1 and 2 with components of the system illustrated in FIGS. 4–9.

Figure 1:
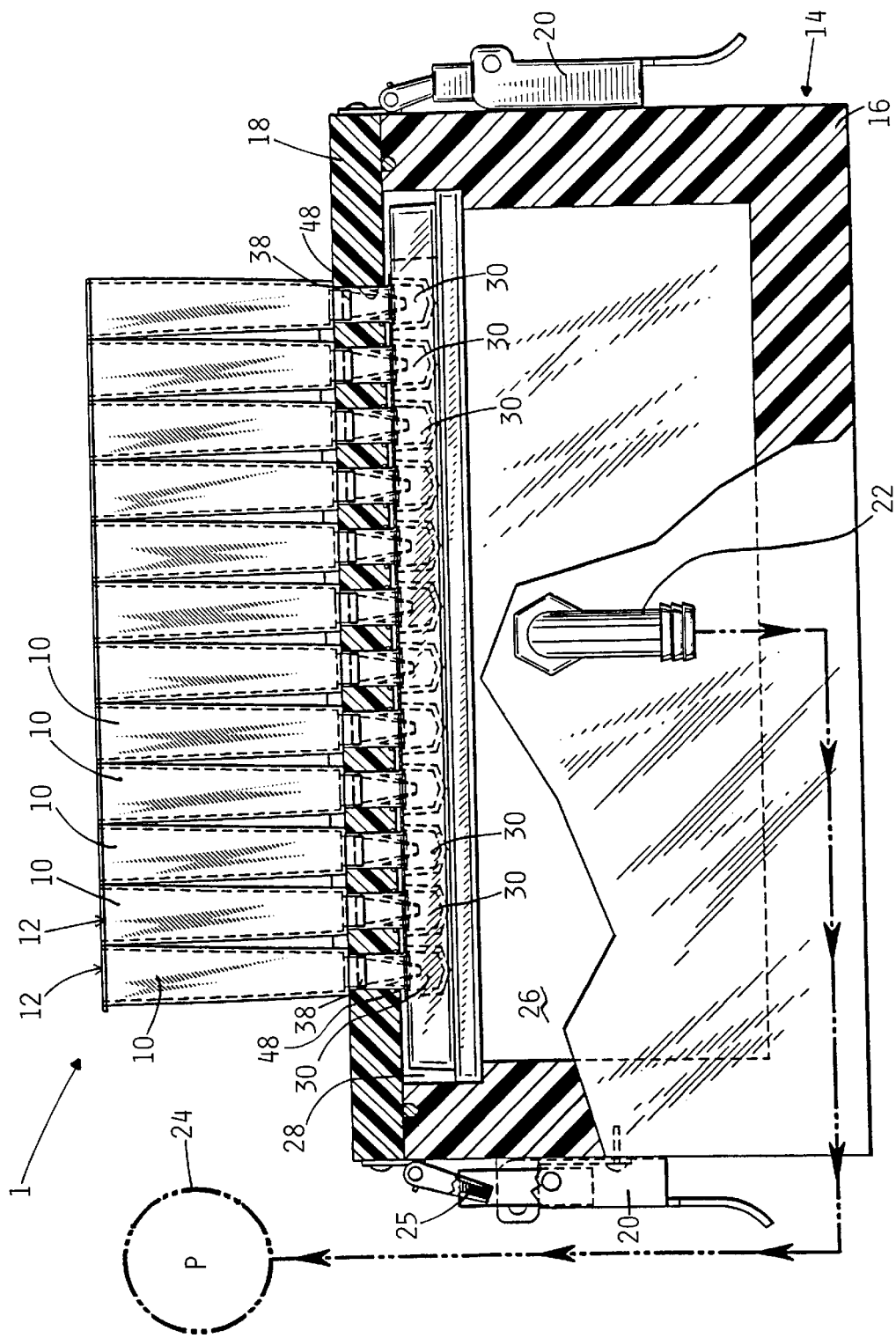
FIG. 1 illustrates a plan view, partially in cross-section, of an embodiment of a filtering system of the present invention.
Figure 2:
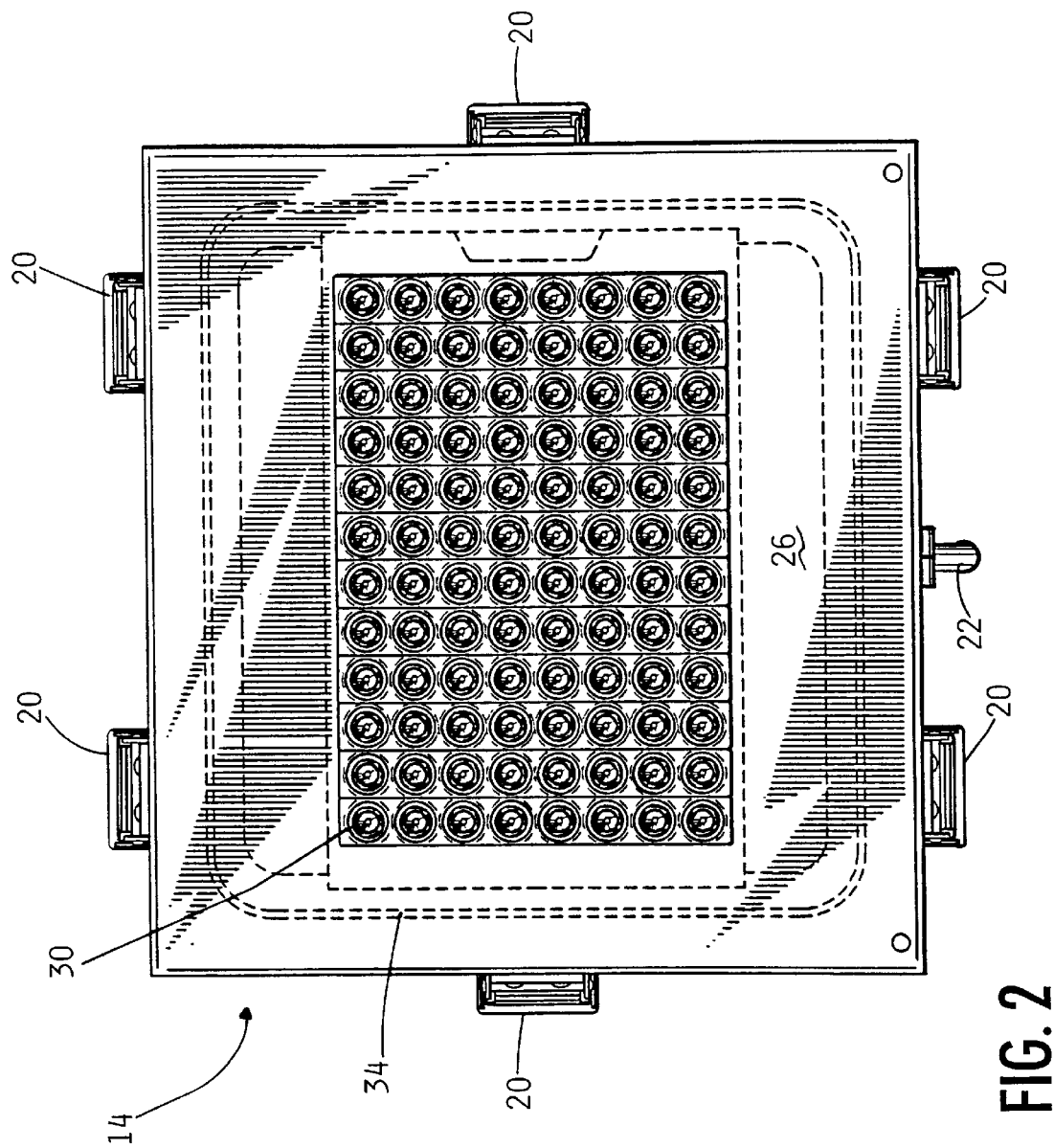
FIG. 2 illustrates a top plan view of an embodiment of a filtering system of the present invention.
Figures 6, 7, 8, 9:
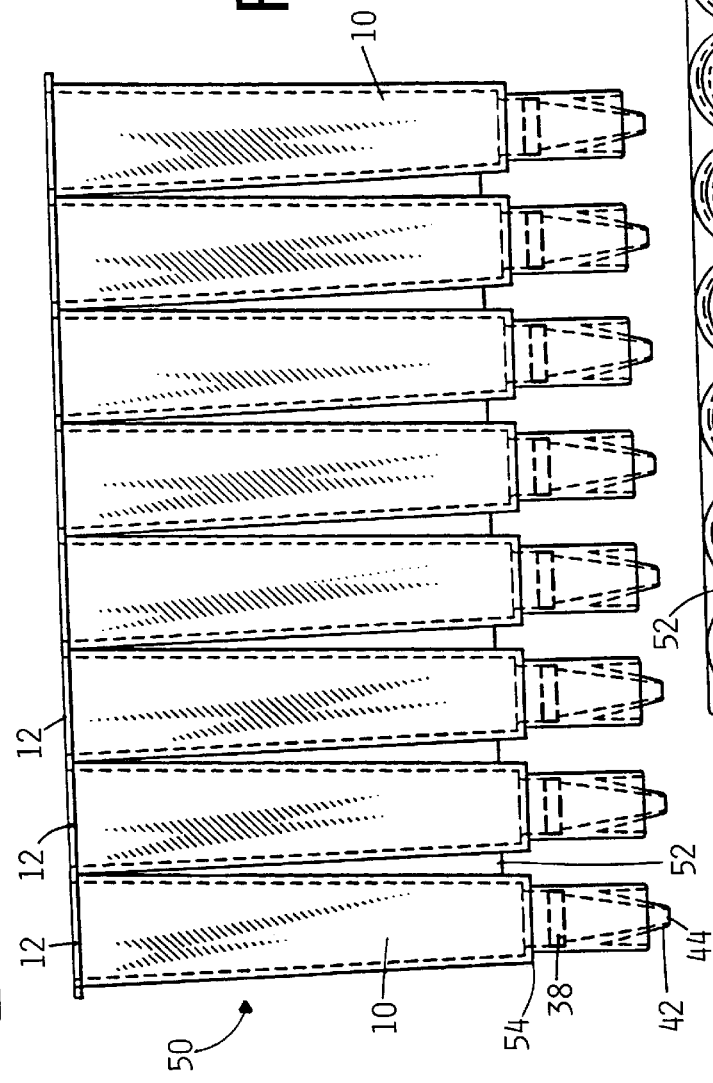
FIG. 6 illustrates a cross-sectional view of an embodiment of a component of the filtering system of the present invention.
FIG. 7 illustrates a plan view of an embodiment of a component of the filtering system of the present invention.
FIG. 8 illustrates a top plan view of an embodiment of the component illustrated in FIG. 7.
FIG. 9 illustrates a bottom plan view of an embodiment of the component illustrated in FIG. 7.

Referring now to the drawings wherein like numerals refer to like parts, FIG. 1 generally illustrates a system 1 for filtering of a sample, such as DNA, from a solution, such as those solutions commonly mixed with DNA or solutions containing DNA to achieve analysis of the DNA following filtering of the DNA from the solution.

To this end, a solution is inserted into each one of a plurality of columns 10. The column 10 includes an opening 12 at each of their top ends. As illustrated, twelve rows of columns are provided in abutted relationship such that solution may easily be provided into each of the openings 12 of the column 10. In a preferred embodiment of the present invention, the columns 10 are connected in rows of eight to form a 12×8 matrix of the columns 10. Of course, one of ordinary skill in the art could produce a different number of columns and rows and the illustrated embodiment shown in the figure is to merely illustrate a preferred embodiment of the present invention.

The system 1 includes a manifold 14 formed from a base 16 and a cover 18. The cover 18 is vacuum sealed to the base 16 of the manifold 14 by means of latches 20. Preferably, the base 16 and the cover 18 are machined from a transparent hard plastic. In another embodiment, the base 16 and the cover 18 may be molded from a transparent hard plastic. This allows the user to verify that a solution is being drawn through the manifold 14 into its interior 26.

In a preferred embodiment, at least one latch 20 is provided on each side of the base 16 with a hook on the cover 18 on which the latch 20 is fastened. As illustrated in FIG. 2, six latches 20 are shown to secure and seal the cover 18 to the base 16. The latches 20 each include at least one spring 25 as illustrated in FIG. 1. The spring 25 maintains a vacuum tight seal between the base 16 and the cover 18 with the assistance of a gasket seal 32.

As further illustrated in FIG. 1, the system 1 includes an inlet 22 for connection to, for example, a fluid line (not shown) and subsequent connection to a pump 24. The pump 24 acts as a vacuum for application to an interior 26 of the manifold 14. The pump 24, therefore, provides a vacuum to the manifold 14 to thereby draw solution contained in each of the columns 10 and to filter the solutions from each of the columns 10.

A filter 38 in each of the columns 10 removes the sample onto a top surface of the filter 38 for analysis following further vacuum of the samples on the filters 38 into a microtiter dish 28 placed in the interior 26 of the manifold 14. The microtiter dish 28 is divided into ninety-six (96) sections or containers 30 corresponding to the ninety-six columns 10 and the corresponding filters 38 in each of the ninety-six columns 10. The microtiter dish 28 can be removed from the manifold 14 for analysis of each of the samples contained within each of the individual containers 30 of the microtiter dish 28. Preferably, the microtiter dish 28 is also transparent such that the user may verify that the containers 30 are being filled as desired.

To this end, following filtration of the solution, the manifold 14 is opened by removing the cover 18. The microtiter dish 28 can be placed on ledges in the interior 26 of the manifold 14 following cleaning of the interior thereof. The cover 18 is then re-secured by latching the cover 18 to the base 16. Water is added to each of the columns 10 which includes the sample on each of the filters 38. The filters 38 are made from a fibrous web that upon reactivation of the pump 24 allows the water with the DNA sample to penetrate the filter 24 as indicated by FIG. 5.

Referring now to FIG. 2, a top plan view of the manifold 14 is illustrated. From this view, each of the containers 30 of the microtiter dish 28 can be clearly seen. To seal the interior 26 of the manifold 14, an O-ring 32 is secured within a recess 34 in a top surface of the base 16 of the manifold 14.

FIG. 3 illustrates a top plan view of the microtiter dish 28. The microtiter dish 28 may include numerical and/or alphabetical labeling for easy referral of a specific container 30 of the microtiter dish 28 corresponding to a sample from a particular column 10. The containers 30 as illustrated are substantially cylindrical with a conical tip 36 at its end as more clearly shown in cross-sectional detail in FIG. 4.

Referring now to FIG. 5, the detail of the connection of a filter 38 within a column 10 with the column 10 inserted into the cover 18 of the manifold 14 is illustrated. To this end, the filter 38 is press-fit into the column 10 to a point where the filter rests on a ledge 40a formed in an interior wall of the column 10. If desired, a larger diameter filter may be employed and seated against an upper ledge 40b. At the ledge 40a, the interior wall of the column 10 begins a taper to a tip 42 having an opening 44 through which the solution in the column 10 is first evacuated into the interior 26 manifold 24 and then the DNA or other sample from the filter 38 is dispensed into the conical tip 36 of the container 30 by suction from the pump 24.

An exterior wall 46 at a bottom section of the column 10 extends from the ledge integral with the interior wall 45 before separating as the interior wall 45 tapers to the tip 42 at the opening 44. The exterior wall 46 forms a sealed relationship with a top of the container with the assistance of an O-ring 48 in an aperture through the cover 18. A sealed relationship is formed following insertion of the exterior wall 46 of each of the columns 10 in a corresponding aperture in the cover 38. The interior wall 45 and the tip 42 further extend into the interior of the container 30.

Prior to suction of the DNA particles with the water placed in the columns 10 from the filter 38, the microtiter dish 28 is placed in the interior 26 of the manifold 14. That is, the solution filtered without containing the DNA is evacuated and is cleaned from the interior 26 of the manifold 14. Then, the vacuum created by the pump 24 through the inlet 22 is used to draw the DNA sample into the containers 30 of the microtiter dish 28 with water added to the sample to assist in penetration of the filter 38.

As previously discussed with reference to FIG. 1, each of the columns 10 is formed as an integral set 50 of a plurality of the columns 10. As illustrated, the columns 10 of the set 50 are in nearly abutting contact between the openings 12 leading into an interior of the columns 10. The columns 10 have an exterior tapering outer wall with a molded piece integrally formed between two adjacent walls of the columns 10 such that the set 50 of the columns 10 results in a substantially rectangular shape, and the columns 10 are maintained in a substantially vertical orientation between a top end with the openings 12 and the openings 44 at the tips 42. The column 10 further has a lip 54 near the end having the tip 42 such that only that portion of each of the columns 10 below the lip 54 is received within an opening in the cover 18 of the vacuum manifold 14.

During some filtering applications, only a portion of the sets 50 of the columns 10 will be used. In such circumstances, a plug (not shown) or tape (not shown) is placed into or over, respectively, each of the holes through the cover 18 of the manifold 14. The plugs or tape maintain a vacuum tight seal within the manifold 14 when only a portion of the sets 50 are used.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for filtering a substance for analysis from a solution, the system comprising:

a plurality of columns capable of receiving the solution with the substance through an inlet end of each of the plurality of columns and dispensing the solution without the substance through an outlet end of each of the plurality of columns;

a filter in each of the plurality of columns;

a manifold having an interior defined by a base portion and a cover, wherein the cover is removably secured to and forms a sealed relationship with the base portion, the cover has a plurality of apertures extending therethrough, each of the plurality of apertures having an interior wall and an o-ring in the interior wall, and each of the plurality of apertures in the cover is adapted to receive the outlet end of one of the plurality of columns and to form a sealed relationship therewith by means of the o-ring; and an inlet connected to the base portion and capable of receiving a connector to provide a vacuum to the interior of the manifold.

2. The system of claim 1, wherein the filter in each of the plurality of columns is capable of capturing the substance from the solution as the solution is dispensed through the outlet end of the plurality of columns.

3. The system of claim 1 wherein at least two of the plurality of columns are integrally formed to form a set of columns.

4. The system of claim 1 wherein the plurality of apertures extending through the cover define an array of rows of the apertures wherein at least a portion of the plurality of columns form a set wherein the number of columns in the set is defined by the number of rows in the array.

5. The system of claim 1 further comprising:

a latch coupling the base portion of the manifold to the cover.

6. The system of claim 1 further comprising:

a seal constructed and arranged between the cover and the base portion of the manifold.

7. The system of claim 1 further comprising:

a ledge formed on an interior wall of the base portion within the interior of the manifold.

8. The system of claim 1 further comprising:

a dish defining a plane having a plurality of containers corresponding to the plurality of apertures in the cover wherein the dish is capable of placement in the interior of the manifold.

9. The system of claim 1 further comprising:

a conical tip within a cylindrical shell leading to the outlet end of each of the plurality of columns wherein each of the apertures in the cover are vertically aligned to receive the cylindrical shell surrounding the conical tip.

10. The system of claim 8 wherein the dish includes designators assisting in identifying each of the plurality of containers in the dish.

11. The system of claim 2 wherein the filter in each of the plurality of columns is capable of capturing a DNA substance from the solution.

12. The system of claim 1 wherein the manifold is constructed from a transparent, molded plastic.

13. The system of claim 5 wherein the latch includes a spring.

14. The system of claim 8 wherein the dish is constructed from a transparent molded plastic.

15. The system of claim 1 wherein the manifold is constructed from a machined plastic.

* * * * *